United States Patent
Stefano

(10) Patent No.: US 8,753,823 B1
(45) Date of Patent: Jun. 17, 2014

(54) IMMUNOASSAY METHOD FOR DETECTING THE PRESENCE OF ANTIBODIES TO INTRAVENOUSLY INJECTED ORAL MEDICATIONS

(76) Inventor: Stephen Stefano, Tampa, FL (US)

( * ) Notice: Subject to any disclaimer, the term of this patent is extended or adjusted under 35 U.S.C. 154(b) by 0 days.

(21) Appl. No.: 13/199,267

(22) Filed: Aug. 24, 2011

Related U.S. Application Data

(60) Provisional application No. 61/402,130, filed on Aug. 24, 2010.

(51) Int. Cl.
*G01N 33/53* (2006.01)

(52) U.S. Cl.
CPC ................................. *G01N 33/53* (2013.01)
USPC .......... 435/7.1; 435/7.92; 435/7.93; 435/7.94; 436/518

(58) Field of Classification Search
None
See application file for complete search history.

(56) References Cited

PUBLICATIONS

Tomashefski et al., Microcrystalline Cellulose Pulmonary Embolism and Granulomatosis, Arch Pathol Lab Med, vol. 105, Feb. 1981, pp. 89-93.*
Shlom et al., Successful lung transplantation for talcosis secondary to intravenous abuse of oral drug, International Journal of COPD, 2008: 3(2), pp. 327-330.*
Gamaleya., Antibodies to drugs as indicators of chronic drug use. An alternative to toxicological hair analysis, Forensic Science International, 63 (1993), pp. 285-293.*

\* cited by examiner

*Primary Examiner* — Gary W Counts

(57) ABSTRACT

The steps of the method are preparing a specific antigen; intravenously injecting prescription medication initially intended for oral consumption into the blood stream of the patient, the prescription medication including an inert binder; creating unnatural antibodies in response to antigenic stimulation; drawing a blood sample from a patient; mixing the drawn blood sample with the prepared specific antigen; and determining the presence of a formation of an antibody-antigen complex indicative of medication initially intended for oral consumption intravenously injected into the blood stream of a patient.

1 Claim, No Drawings

IMMUNOASSAY METHOD FOR DETECTING THE PRESENCE OF ANTIBODIES TO INTRAVENOUSLY INJECTED ORAL MEDICATIONS

RELATED APPLICATION

This application claims the benefit of Provisional Application Ser. No. 61/402,130 filed Aug. 24, 2010 the subject matter of which is incorporated herein by reference.

BACKGROUND OF THE INVENTION

1. Field of the Invention

The present invention relates to an immunoassay method for detecting the presence of antibodies to intravenously injected oral medications and more particularly pertains to detecting that certain narcotics have been injected into the blood stream of a patient.

2. Description of the Prior Art

The use of medication detection systems of known designs and configurations is known in the prior art. More specifically, drug detection systems of known types previously devised and utilized for the purpose of detecting certain drug uses are known to consist basically of familiar, expected and obvious method configurations, notwithstanding the myriad of designs encompassed by the crowded prior art which has been developed for the fulfillment of countless objectives and requirements.

While these devices fulfill their respective, particular objectives and requirements, the patent literature does not describe a method for detecting the presence of antibodies to intravenously injected oral medications that allows detecting that certain types of drugs have been injected into the blood stream of a patient.

In view of the absence of any objective blood test to determine the intravenous injection of narcotic medications intended for oral consumption, the present invention provides an new method for the detection of intravenously injected oral narcotic medications. As such, the general purpose of the present invention, which will be described herein, is a method for the detection of certain specific antibodies to inert ingredients commonly used in the formation of narcotic medications intended for oral consumption, when used intravenously.

In this respect, the method for the detection of oral medications injected into the blood stream of a patient according to the present invention substantially departs from the conventional concepts and methods of the prior art, and in doing so provides an immunoassay method primarily developed for the purpose of detecting, through indirect immunoassay means, that orally prepared medications have been injected into the blood stream of a patient.

Therefore, it can be appreciated that there exists a continuing need for a new and improved method for the detection of intravenously injected oral medications which can be used for detecting that certain types of narcotics have been injected into the blood stream of a patient. In this regard, the present invention substantially fulfills this need.

SUMMARY OF THE INVENTION

In view of the disadvantages inherent in the known types of medications detection systems of known designs and configurations now present in the prior art, the present invention provides an improved method for the detection of intravenously injected oral medications. As such, the general purpose of the present invention, which will be described as an immunoassay method, is for the detection of certain narcotics injected into the blood stream of a patient which has all the advantages of the prior art and none of the disadvantages.

In this respect, before explaining at least one embodiment of the invention in detail, it is to be understood that the invention is not limited in its application to the details of the steps set forth in the following description. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other methods and systems for carrying out the several purposes of the present invention. It is important, therefore, that the invention be regarded as including such equivalent methods insofar as they do not depart from the spirit and scope of the present invention.

For a better understanding of the invention, its operating advantages and the specific objects attained by its uses, reference should be had to the accompanying descriptive matter in which there is explained a preferred embodiment of the invention.

DESCRIPTION OF THE PREFERRED EMBODIMENT

The preferred embodiment of the new and improved immunoassay method for the detection of injected oral medications in the blood stream of a patient embodying the principles and concepts of the present invention will be described.

By way of background, antibody testing usually involves mixing a patient's blood sample with a known antigen. An antigen is a substance that the antibody is directed against, or introduced in response to, and determining if a reaction takes place. If an antibody is present and binds to the known antigen, the formulation of the antibody-antigen complex can be identified and measured.

The present invention, the immunoassay method for the detection of intravenously injected oral medications, is comprised of a plurality of steps. Such steps are individually configured and correlated with respect to each other so as to attain the desired objective. In their broadest context, such steps include preparing a specific antigen, intravenously injecting medications, creating unnatural antibodies, drawing blood, mixing the blood sample with the antigen and determining the presence of a formation of an antibody-antigen complex. In this context, the invention includes the steps of:

1. The first step is the preparing of a specific antigen derived from the inert ingredients common to oral narcotic medications.

2. Narcotic pain medication in the pill form is composed of both the active narcotic medication and inactive, inert ingredients. The narcotic medication has been applied to the inactive, inert ingredients. These inactive, inert components (cellulose, lactulose, magnesium stearate, etc.) allow for this mixture of both narcotic medication and inert ingredients to be compressed into a pill form allowing for self-administration orally of a predetermined amount of narcotic pain medication. The inactive, inert ingredients dissolve as the pill passes through the gastrointestinal track, liberating the narcotic medication held within which is then absorbed by the intestinal cells, and into the blood stream. The inactive, inert ingredients, however, are not absorbed and continue to pass through the intestines and into the stool. The present invention does not seek to determine a narcotic drug level; both oral and intravenous use will lead to a measurable drug level. The present invention does seek to determine if the narcotic medication pill, which was developed only for oral consumption, has been abused by injecting it intravenously. The present invention seeks to identify if intravenous abuse of a narcotic medication which was intended for oral use only has occurred. This is done by identifying antibodies developed by a person who has injected intravenously the narcotic which was intended for oral use.

3. The third step is creating unnatural antibodies in the patient, and by the patient, in response to antigenic stimulation caused by the intravenous injection of the inert binder.

4. The fourth step is drawing a blood sample from a patient, a patient who is suspected of intravenously injecting the prescription medications. The prescription medications was initially intended for oral consumption.

5. The fifth step is mixing the drawn blood sample with the prepared specific antigen.

6. The sixth and last step of the method of the present invention is determining the presence of a formation of an antibody-antigen complex. In this manner a presence of such formulation is determined. A presence of such formulation is indicative of the presence of the inert binder in the blood stream and hence, by implication, the intravenous injection of medications initially intended for oral consumption. Further in this manner an absence of such formulation may be determined. Absence of such formulation is indicative of the absence of the inert binder in the blood stream and hence, by implication, the absence of intravenous injection of medications initially intended for oral consumption.

From the foregoing, it may be appreciated that the present invention relates to an immunological blood test. Such test is adapted to determine the presence of unnatural antibodies. Such antibodies are created in the patient, by the patient, in response to antigenic stimulation. Antigenic stimulation is caused by specific inert ingredients common to oral prescription narcotics when injected intravenously. Thus provided is the objective indirect likelihood of intravenous abuse of oral narcotic medications.

Results from testing in accordance with the method of the present invention include:

1. Antibodies to these specific inert ingredients are not present in individual who have not intravenously injected narcotics prepared for oral consumption.

2. Antibodies to these specific inert ingredients are not present in individual who have received narcotic medications or other medications prepared for and intended for oral intravenous administration.

3. Antibody titer to these specific inert ingredients are reflective of and relative to the time and amount of oral narcotics injected intravenously in the immuno-competent patient.

4. The antibody test has a high sensitivity and specificity for the inert ingredients of oral narcotic medications likely to be abused intravenously. Such antibody test is able to be evaluate both qualitatively and quantitatively.

As to the manner of usage and operation of the present invention, the same should be apparent from the above description. Accordingly, no further discussion relating to the manner of usage and operation will be provided.

With respect to the above description then, it is to be realized that the optimum relationships for the steps of the invention, to include variations in materials, form, function and manner of operation and use, are deemed readily apparent and obvious to one skilled in the art, and all equivalent relationships to those described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact method steps, construction and operation shown and described, and accordingly, all suitable modifications and equivalents may be resorted to, falling within the scope of the invention.

What is claimed is:

1. A method for the detection of intravenous abuse of oral narcotic medication in a patient, the medication being initially intended for oral consumption, the method comprising, in combination, the steps of:

preparing a specific antigen derived from an inert binder;

intravenously injecting prescription medication initially intended for oral consumption into the blood stream of the patient, the prescription medication including the inert binder;

producing unnatural antibodies in the patient, and by the patient, in response to antigenic stimulation caused by the intravenous injection of the inert binder;

drawing a blood sample from the patient;

mixing the drawn blood sample with the prepared specific antigen; and detecting the presence of a formation of an antibody-antigen complex comprising the unnatural antibodies and the specific antigen indicative of intravenous abuse of medication intended for oral conception only.

* * * * *